United States Patent [19]

Mailliet et al.

[11] Patent Number: 5,108,192
[45] Date of Patent: Apr. 28, 1992

[54] PROBE FOR TAKING GAS SAMPLES AND HEAT MEASUREMENTS IN A SHAFT FURNACE

[75] Inventors: Pierre Mailliet, Howald; Emile Lonardi, Bascharage; Georges Wies, Dudelange, all of Luxembourg

[73] Assignee: Paul Wurth S.A., Luxembourg, Luxembourg

[21] Appl. No.: 663,138

[22] Filed: Mar. 1, 1991

[30] Foreign Application Priority Data

Mar. 7, 1990 [LU] Luxembourg .................... 87693

[51] Int. Cl.⁵ ............................................ G01K 13/02
[52] U.S. Cl. ........................... 374/139; 136/230; 136/238; 374/166; 374/208
[58] Field of Search ................ 374/139, 141, 140, 137; 136/230, 234; 73/292

[56] References Cited

U.S. PATENT DOCUMENTS

| 3,247,714 | 4/1966 | Schwabe et al. | 374/139 x |
| 3,834,237 | 9/1974 | Robertson | 136/230 x |
| 3,923,552 | 12/1975 | Parris | 136/234 |
| 3,946,610 | 3/1976 | Sattorius | 374/139 X |
| 4,919,543 | 4/1990 | Davis et al. | 374/140 |

*Primary Examiner*—Daniel M. Yasich
*Attorney, Agent, or Firm*—Fishman, Dionne & Cantor

[57] ABSTRACT

The probe comprises a support in the form of a sheath, a series of internal pipes, retained by spacers and connecting orifices distributed along the sheath to a device for measuring and for receiving the gas samples outside the furnace, and thermocouples arranged at the level of the said orifices. In order to enable the pipes to be replaced without disassembly of the probe, the said orifices are situated in steps provided in the sheath, while the internal pipes, for taking gas samples and heat measurements are all individual, straight and exchangeable elements housed in straight support and protection channels, each traversing the sheath from the outside as far as the respective step.

6 Claims, 5 Drawing Sheets

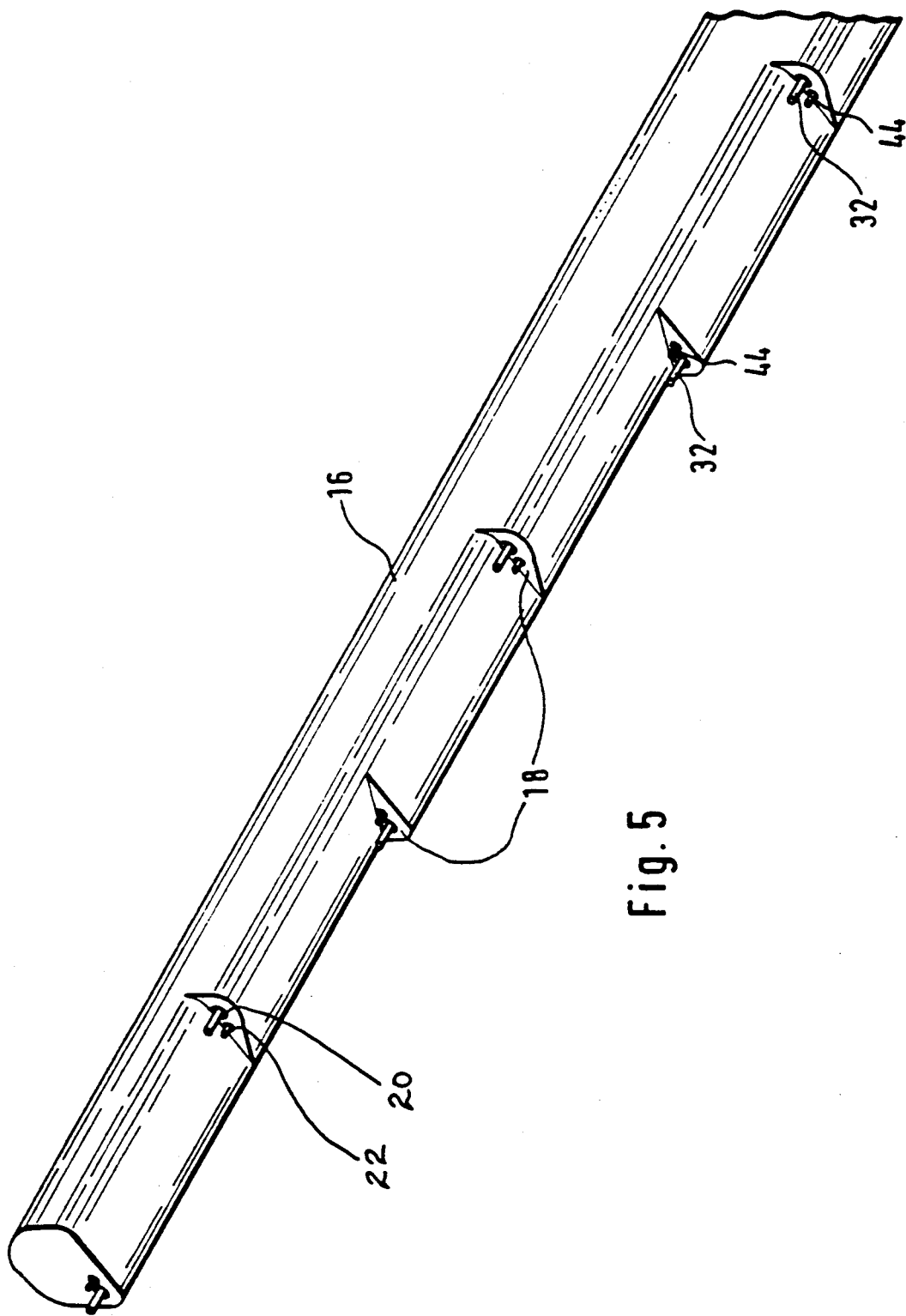

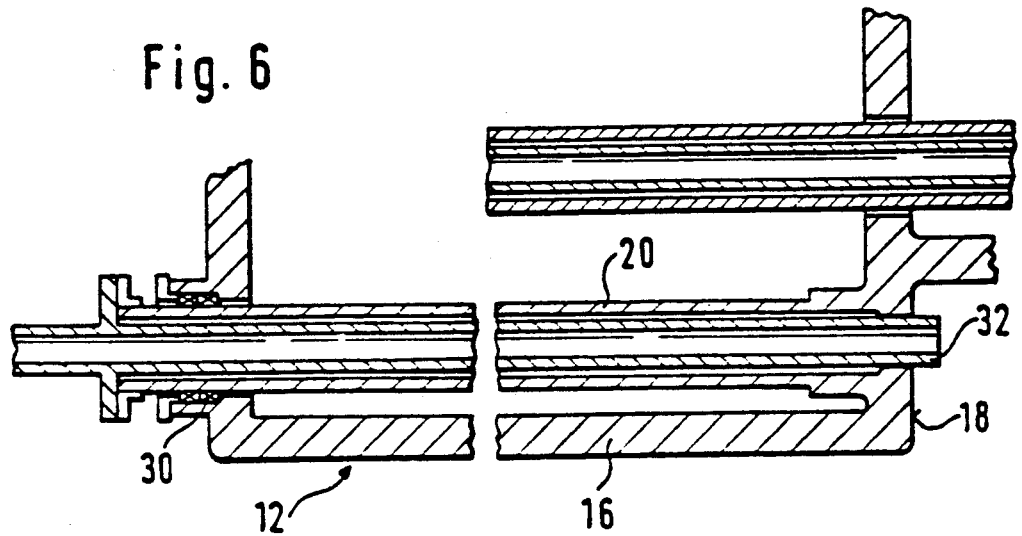
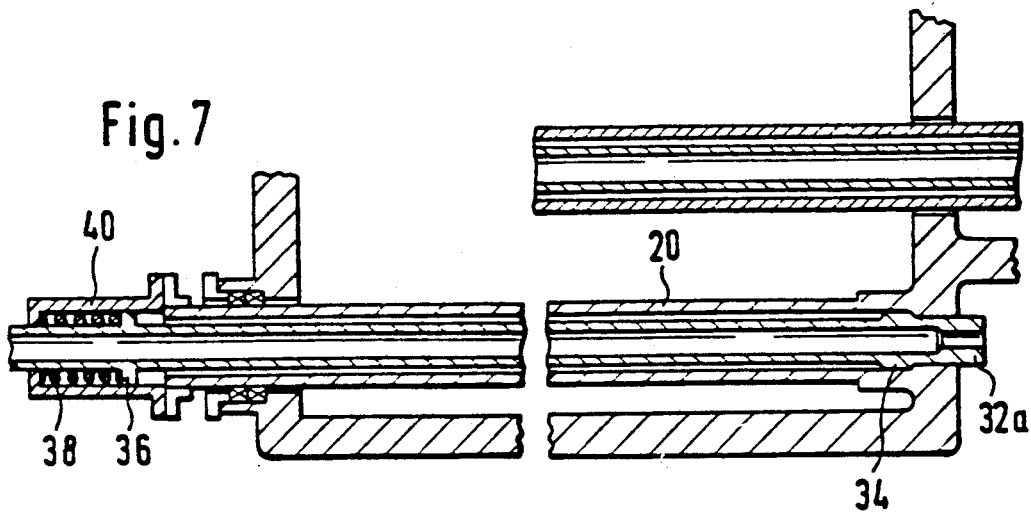
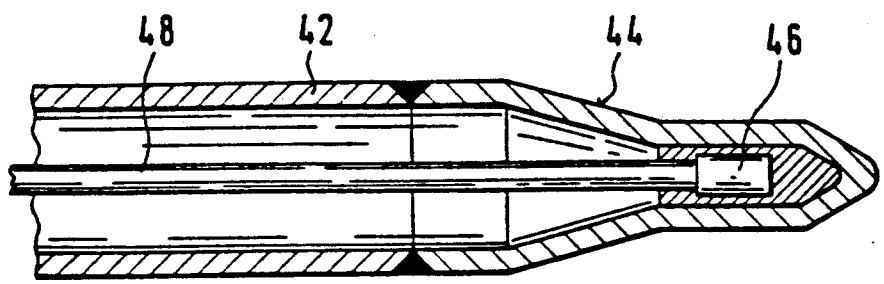

PROBE FOR TAKING GAS SAMPLES AND HEAT MEASUREMENTS IN A SHAFT FURNACE

TECHNICAL FIELD

The present invention relates to a probe for taking gas samples and heat measurements in a shaft furnace.

BACKGROUND OF THE INVENTION

U.S. Pat. No. 3,130,584 describes a probe for taking gas samples and heat measurements in a shaft furnace.

Given the extremely severe working conditions of these probes, they require frequent maintenance, for example in order to replace a faulty thermocouple or unplug a blocked pipe for taking gas samples. In order to carry out these maintenance operations, it was hitherto necessary to disassemble the probe completely and to carry out this work, more often than not, in the repair shop, which, of course, constitutes a loss of time.

SUMMARY OF THE INVENTION

The object of the present invention is to provide a novel probe which permits the "in-situ" replacement of the pipes for taking gas samples and heat measurements without disassembly of the probe.

In order to achieve this objective, the present invention proposes a probe essentially comprising a support in the form of a sheath introduced through the wall of the furnace above the charging surface, a series of internal pipes connecting orifices distributed along the sheath to a device for measuring and for receiving the gas samples outside the furnace, thermocouples arranged at the level of the said orifices, spacers placed transversely in the sheath in the sheath in order to retain the internal pipes, and one or more cooling circuits traversing the sheath.

In is preferred embodiment, the probe is essentially characterized in that the surface areas of the spacers decrease gradually from the wall of the furnace to the tip of the probe, in that the difference in surface area between two adjacent spacers defines an exposed portion of the larger spacer and a corresponding, transversely narrowing step of the sheath, in that the said orifices are situated in the said exposed portions, and in that the internal pipes for taking gas samples and heat measurements are all individual, straight and exchangeable elements housed in straight support and protection channels each traversing the sheath from the outside as far as the respective exposed portion.

According to a preferred embodiment, the said exposed portions of the spacers have a substantially triangular shape, the tip being turned towards the charging surface, whereas the various successive triangular portions are in a staggered arrangement, relative to one another, when viewed in axial projection.

Each of the internal pipes can be flange-mounted directly onto the sheath outside the furnace. The pipes can also be retained in place in their support channel via a helical spring outside the furnace.

The inner end of each heat-measurement pipe comprises a closed tip in which is housed a thermocouple embedded in a material with good thermal conductivity, and connected via the pipe to the heat-measurement device outside the furnace.

BRIEF DESCRIPTION OF THE DRAWINGS

Other features and characteristics of the invention will become apparent from the description of some advantageous embodiments given below, by way of illustration, with reference to the attached drawings, in which:

FIG. 5 shows diagrammatically a perspective view of a part of the probe;

FIG. 6 shows diagrammatically a partial vertical section of a first embodiment of the arrangement of the sampling pipes;

FIG. 7 shows a view similar to that in FIG. 6 of a second embodiment of the sampling pipes, and FIG. 8 shows diagrammatically the inner end of the heat-measurement pipes.

DETAILED DESCRIPTION OF THE INVENTION

Figure 1:
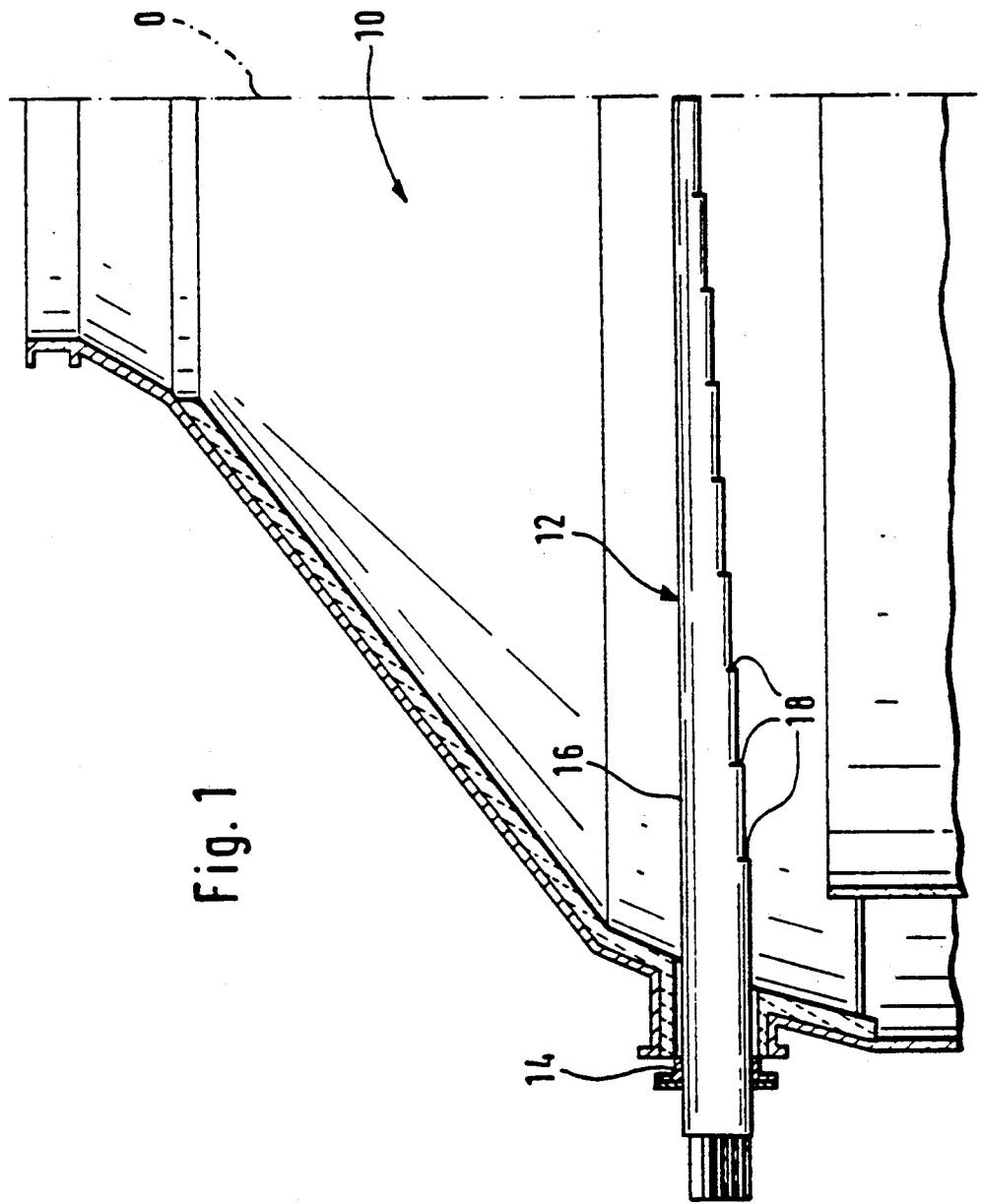
FIG. 1 shows diagrammatically a first embodiment of a probe according to the present invention.
Figure 4:
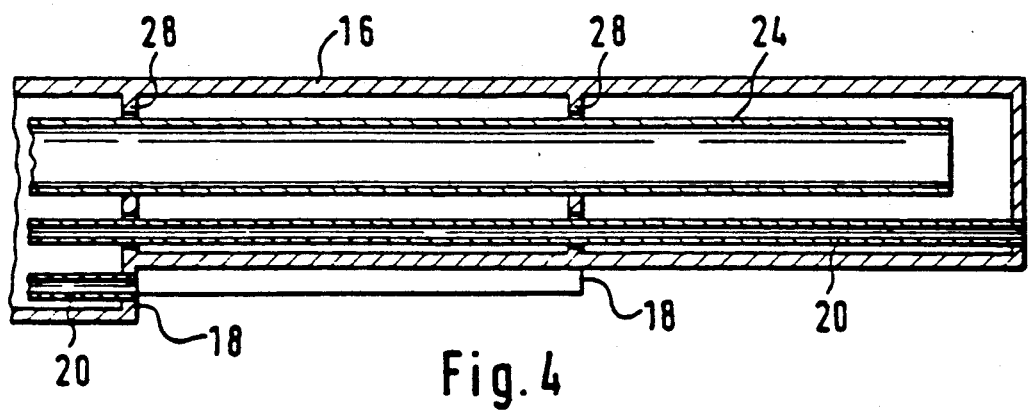
FIG. 4 shows a section of the inner end of the probe along the plane of section A—A in FIG. 3.

FIG. 1 shows diagrammatically a part of the head of a shaft furnace 10. The reference 12 designates a probe for heat measurements and for taking gas samples which is retained in a support 14 of the wall of the furnace and which extends horizontally above the charging surface as far as the central axis of the furnace. This probe includes an outer sheath 16 in FIG. 4 shows, in section, the inner end of the probe 12 with the penultimate and last of the steps 18, the latter being only partly visible since it is arranged beyond the vertical plane of symmetry. This figure shows a straight channel 20 opening out at the end of the sheath 16 and a second similar channel opening out in the radial face of the penultimate step 18, another similar channel opening out in the last step 18 but not being visible in FIG. 4. The channels 20 are supported, inside the sheath 16, by transverse spacers 28 which are integral with the sheath 16 and which each form the radial face of each of the steps 18. The spacers 28 also support, inside the sheath 16, the axial channel 24, or possibly a plurality of channels, for the circulation of the cooling liquid. This cooling liquid, which may simply be water, fills the whole sheath 16 and circulates around the channels 20 through non-sealed passages in the spacers 28 around the channels 20, 22 and 24, or through additional perforations in the spacers, as far as the tip of the sheath 16 and then returns to the outside through the axial channel 24. The channels 22 not visible in FIG. 4 are similar to the channels 20 and run parallel to the latter through the sheath 16 and the spacers 28.

One of the features of the present invention is to permit the introduction of the means for taking gas samples and heat measurements into each of the channels 20, 22 from outside the probe 12 without having to remove the probe 12 from the furnace and without having to empty the cooling circuit, which are arranged pipes for taking gas samples and heat measurements which, in accordance with the present invention, are all individual, straight and exchangeable elements which each end in one of the steps 18 formed in the sheath 16 over the entire length of the probe and giving the latter a tapered shape.

Figure 2:
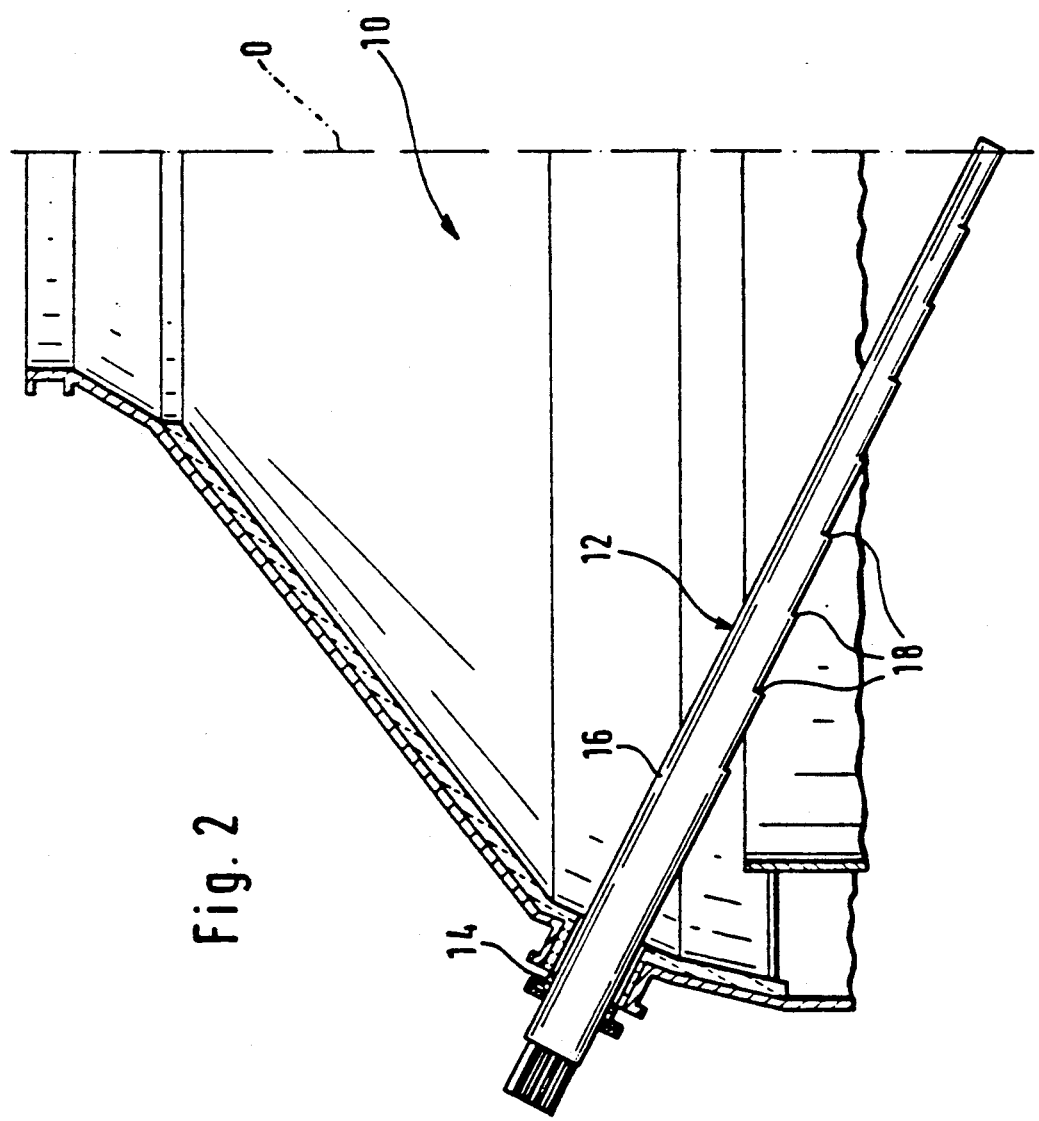
FIG. 2 shows diagrammatically a second embodiment of a probe according to the present invention.

FIG. 2 shows a probe 12 whose structure is identical to that in FIG. 1 but which is inclined with respect to the horizontal, the head of the probe 12 being lower than the support 14. This arrangement has been selected so that the probe 12 is parallel to the charging surface in furnaces which operate with a "V-shaped" charging profile.

Figure 3:
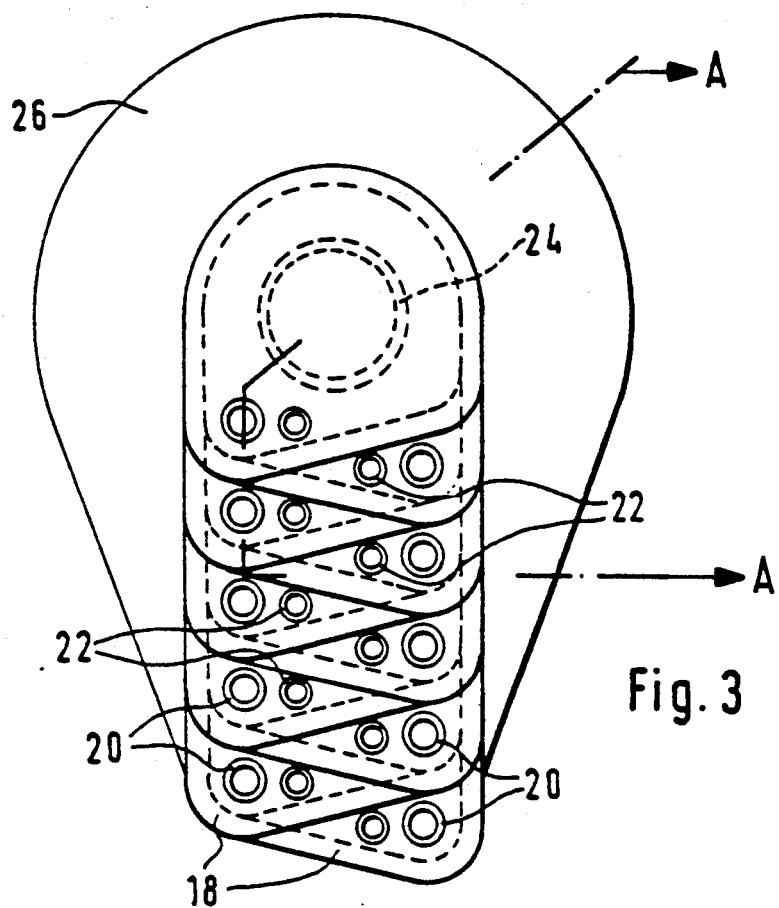
FIG. 3 shows diagrammatically an axial view of the probe from inside the furnace.

The special appearance of the probe 12 in the form of steps is clearly apparent from FIGS. 3 and 5. As shown in the perspective view of FIG. 5, the section of the probe 12 decreases gradually from the outside towards the inside in successive steps 18 arranged radially with respect to the axis of the probe and into which open channels 20, 22 provided respectively for taking gas samples and heat measurements. As shown in FIG. 3, the steps 18 have a substantially triangular shape. They are provided alternately on either side of a vertical plane passing through the axis of the probe. The reference 24 in FIG. 3 designates an axial channel for the circulation of a cooling liquid, and the reference 26 designates a protecting cover which is normally provided around the upper part of the probe and which can consist, for example, in a manner known per se, of stone boxes.

FIG. 6 shows in more detail one of the internal channels 20 extending from one of the steps 18 as far as the outside of the furnace, leaving the sheath 16 via a seal 30 enabling the cooling liquid to be contained in a sealed manner inside the sheath 16 as well as the differential expansions between the sheath 16 and the channel 20. The channel 20 shown in FIG. 6 contains a pipe 32 extending over the entire length of the channel 20 and emerging in the radial face of one of the steps 18. The pipe is in this case one for taking gas samples, it being possible for the gases to penetrate at the level of the step 18 into the pipe 32 and to traverse the latter in order to be collected outside the furnace with a view to analyses. In the embodiment of FIG. 6, the pipe 32 is flange-mounted outside the probe 12 onto the channel 20. The inner end, on the other hand, emerges freely from the channel 20 so as to permit differential thermal expansions and to facilitate disassembly. Indeed, with a view to this disassembly, it is sufficient to unbolt the pipe 32 outside the furnace and to disengage it freely from its channel 20 without disturbing the operation of the remainder of the probe. It is also possible to unplug it be engaging a rod from outside.

FIG. 7 shows a second embodiment, for positioning and retaining a pipe 32a for taking gas samples. This pipe 32a is likewise engaged freely through the channel 20, but this pipe 32a comprises, at its inner end, an enlargement 34 which interacts with the inner end of the channel 20 in order to define the operating position of the pipe 32a. Outside the probe 12, the pipe 32a comprises a peripheral flange 36 which is stressed elastically, in the penetrating direction, into the channel 20 by a helical spring 38 arranged around the pipe 32a and bearing on the base of a cap 40 which is bolted onto the outer part of the channel 20 or onto the sheath 12. The pipe 32a is therefore retained in place elastically, the spring 38 enabling the differential thermal expansions to be compensated. For disassembly, it is likewise sufficient simply for the cap 40 to be unbolted and the pipe 32a removed.

FIG. 8 illustrates a pipe 42 for heat measurements. This pipe 42 is engaged and fixed in the corresponding channel 22 in the same way as the pipe 32 according to FIG. 6 or the pipe 32a according to FIG. 7. At the inner end of each of the pipes 42, a cover 44 is welded in the form of a closed tip containing a thermocouple 46 embedded in a material having good thermal conductivity. Each thermocouple 46 is connected electrically by a rod 48 through its pipe 42 to the measuring device outside the furnace. In the operating position, the pipes 42 are retained in their channel 22 in such a way that the cover 44 emerges from the wall of the sheath 16 forming the corresponding step, as shown in the perspective view in FIG. 5.

While preferred embodiments have been shown and described, various modifications and substitutions may be made thereto without departing from the spirit and scope of the invention. Accordingly, it is to be understood that the present invention has been described by way of illustrations and not limitations.

What is claimed is:

1. A probe for taking gas samples and heat measurements above a charging surface of a shaft furnace, said shaft . furnace including a furnace wall, comprising:

outer sheath means for inserting into said furnace through an opening in said furnace wall, said sheath means extending longitudinally from a first end, said first end to be mounted outside of said furnace wall, to a second end said second end to be positioned within said furnace and above said charging surface, and said sheath means exhibiting a cross sectional area which stepwise decreases with distance from the first end to the second end;

a plurality of transverse spacers longitudinally spaced apart within the sheath means, each of said spacers exhibiting an exposed portion, said exposed portions defining a plurality of longitudinally spaced apart transverse steps for narrowing the sheath means and said exposed portions defining a plurality of orifices therethrough, a plurality of channels supported within said sheath means, each of said channels extending longitudinally from the first end of the sheath means to a respective one of the transverse steps;

a plurality of longitudinally extending internal pipes, each of said pipes being removably secured within a respective one of the channels to connect a respective one of said orifices to a device for measuring and receiving gas samples; and a plurality of thermocouples, each removably received within a respective one of said channels for measuring temperature at a respective one of said steps.

2. The probe of claim 1, wherein the exposed portions of the spacers each have a substantially triangular shape and wherein the successive exposed portions are disposed in a staggered arrangement, relative to each other, when the probe is viewed in axial projection.

3. The probe of claim 1, further comprising a plurality of flanges for mounting the internal pipes to the first end of the sheath means.

4. The probe of claim 1, further comprising resilient means for retaining the internal pipes within their respective channels.

5. The probe of claim 1, wherein the sheath means forms a sealed shell, wherein the channels are sealing secured within the shell and wherein the sealed shell is connected to a cooling circuit.

6. The probe of claim 5, further comprising one or more cooling channels, supported within said sheath means, for circulating a cooling fluid within the shell.

* * * * *

UNITED STATES PATENT AND TRADEMARK OFFICE
CERTIFICATE OF CORRECTION

PATENT NO. : 5,108,192

DATED : April 28, 1992

INVENTORS : Pierre Mailliet et al

It is certified that error appears in the above-identified patent and that said Letters Patent is hereby corrected as shown below:

Col. 1, line 34, Delete "in the sheath", second occurrence.

Col. 1, line 37, Delete "In is" and insert therefor --In a--.

Col. 2, line 31, At the end of the paragraph, insert --which are arranged pipes for taking gas samples and heat measurements which, in accordance with the present invention, are all individual, straight and exchangeable elements which each end in one of the steps 18 formed in the sheath 16 over the entire length of the probe and giving the latter a tapered shape.--

Following this paragraph, insert two new paragraphs:

--Figure 2 shows a probe 12 whose structure is identical to that in Figure 1 but which is inclined with respect to the horizontal, the head of the probe 12 being lower than the support 14. This arrangement has been selected so that the probe 12 is parallel to the charging surface in furnaces which operate with a "V-shaped" charging profile.

The special appearance of the probe 12 in the form of steps is clearly apparent from Figures 3 and 5. As shown in the perspective view of Figure 5, the section of the probe 12 decreases gradually from the outside towards the inside in successive steps 18 arranged radially with respect to the axis of the probe and into which open channels 20, 22 provided respectively for taking gas samples and heat measurements. As shown in Figure 3, the steps 18 have a substantially triangular shape. They are provided alternately on either side of a vertical plane passing through the axis of the probe. The reference 24 in Figure 3 designates an axial channel for the circulation of a cooling liquid, and the reference 26 designates a protecting cover which is normally provided around the upper part of the probe and which can consist, for example, in a manner known per se, of stone boxes.--

UNITED STATES PATENT AND TRADEMARK OFFICE
CERTIFICATE OF CORRECTION

PATENT NO. : 5,108,192

DATED : April 28, 1992

INVENTORS : Pierre Mailliet et al

It is certified that error appears in the above-identified patent and that said Letters Patent is hereby corrected as shown below:

Col. 2, line 60 through Col. 3, line 22, Delete "which are arranged pipes for taking gas samples and heat measurements which, in accordance with the present invention, are all individual, straight and exchangeable elements which each end in one of the steps 18 formed in the sheath 16 over the entire length of the probe and giving the latter a tapered shape.

Figure 2 shows a probe 12 whose structure is identical to that in Figure 1 but which is inclined with respect to the horizontal, the head of the probe 12 being lower than the support 14. This arrangement has been selected so that the probe 12 is parallel to the charging surface in furnaces which operate with a "V-shaped" charging profile.

The special appearance of the probe 12 in the form of steps is clearly apparent from Figures 3 and 5. As shown in the perspective view of Figure 5, the section of the probe 12 decreases gradually from the outside towards the inside in successive steps 18 arranged radially with respect to the axis of the probe and into which open channels 20, 22 provided respectively for taking gas samples and heat measurements. As shown in Figure 3, the steps 18 have a substantially triangular shape. They are provided alternately on either side of a vertical plane passing through the axis of the probe. The reference 24 in Figure 3 designates an axial channel for the circulation of a cooling liquid, and the reference 26 designates a protecting cover which is normally provided around the upper part of the probe and which can consist, for example, in a manner known per se, of stone boxes."

Col. 3, line 36, Delete "FIG. 6." and insert therefor --FIG. 6,--.

Col. 3, line 44, Delete "be" and insert therefor --by--.

UNITED STATES PATENT AND TRADEMARK OFFICE
CERTIFICATE OF CORRECTION

PATENT NO. : 5,108,192

DATED : April 28, 1992

INVENTORS : Pierre Mailliet et al

It is certified that error appears in the above-identified patent and that said Letters Patent is hereby corrected as shown below:

Col. 4, line 35, Delete "therethrough," and insert therefor --therethrough;--.

Col. 4, line 39 Delete "steps:" and insert therefor --steps;--.

Signed and Sealed this

Eighth Day of February, 1994

Attest:

BRUCE LEHMAN

Attesting Officer    Commissioner of Patents and Trademarks